(12) United States Patent
Yu et al.

(10) Patent No.: US 10,816,448 B2
(45) Date of Patent: Oct. 27, 2020

(54) DEVICE FOR MEASURING STRENGTH AND STRAIN SOFTENING PARAMETERS OF SATURATED CLAY SAMPLE BASED ON FULL-FLOW PENETRATION

(71) Applicant: DALIAN UNIVERSITY OF TECHNOLOGY, Liaoning (CN)

(72) Inventors: Long Yu, Liaoning (CN); Yunrui Han, Liaoning (CN); Qing Yang, Liaoning (CN); Zhongtao Wang, Liaoning (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 0 days.

(21) Appl. No.: 16/652,791

(22) PCT Filed: Aug. 31, 2019

(86) PCT No.: PCT/CN2019/103886
§ 371 (c)(1),
(2) Date: Apr. 1, 2020

(87) PCT Pub. No.: WO2020/048408
PCT Pub. Date: Mar. 12, 2020

(65) Prior Publication Data
US 2020/0249139 A1    Aug. 6, 2020

(30) Foreign Application Priority Data
Sep. 4, 2018    (CN) .......................... 2018 1 1023958

(51) Int. Cl.
*G01N 33/24* (2006.01)
*G01N 3/42* (2006.01)
*G01N 3/48* (2006.01)

(52) U.S. Cl.
CPC ............... *G01N 3/48* (2013.01); *G01N 33/24* (2013.01); *G01N 2203/0005* (2013.01); *G01N 2203/0019* (2013.01); *G01N 2203/0032* (2013.01)

(58) Field of Classification Search
CPC .... G01N 33/24; G01N 33/241; G01N 33/246; G01N 2033/243; G01N 2033/245; G01N 2033/248; E02D 33/00
See application file for complete search history.

(56) References Cited

U.S. PATENT DOCUMENTS 3,608,367 A * 9/1971 Karol ........................ G01N 3/10
                                                      73/825
3,610,035 A * 10/1971 Handy .................... E02D 1/022
                                                      73/784

(Continued)

FOREIGN PATENT DOCUMENTS

| CN | 106053205 A | 10/2016 |
| CN | 109030182 A | 12/2018 |

(Continued)

OTHER PUBLICATIONS

Xia Han et al, "Evaluation Method of Soft Soil Strength Characteristics based on Full Flow Penetration Probe" Chinese Journal of Underground Space and Engineering; vol. 12, Dec. 15, 2016, pp. 619-624.

*Primary Examiner* — Herbert K Roberts
(74) *Attorney, Agent, or Firm* — Muncy, Geissler, Olds & Lowe, P.C.

(57) ABSTRACT

A device for measuring strength and strain softening parameters of a saturated clay sample based on full-flow penetration belongs to the technical field of geotechnical, geological and environmental research. The device mainly comprises two parts: an overlying pressure loading system and a full-flow penetration system. The present invention mainly aims at the problem of incomplete backflow of the soil in the measurement of soil strength and strain softening parameters with a full-flow penetrometer for saturated clay, and applies the working principle of a traditional consolidometer to vertically pressurize a soil sample to ensure the backflow of the soil, thereby improving the applicability of the full-flow penetrometer in the measurement aspect of the soil strength and the strain softening parameters and having important (Continued)

practical value for test research and marine engineering design.

1 Claim, 3 Drawing Sheets

(56) References Cited

U.S. PATENT DOCUMENTS

| | | | |
|---|---|---|---|
| 4,492,111 A | 1/1985 | Kirkland | |
| 5,253,518 A * | 10/1993 | Steiger | E21B 49/006 166/250.01 |
| 5,591,902 A * | 1/1997 | Castagner | E02D 1/022 73/82 |
| 2005/0177309 A1* | 8/2005 | Sri Ranjan | G01N 1/08 73/38 |
| 2009/0000361 A1* | 1/2009 | Bloomquist | G01N 3/24 73/86 |
| 2018/0120283 A1* | 5/2018 | Gupta | G01N 33/24 |
| 2018/0340417 A1* | 11/2018 | Cooper | E21B 49/02 |

FOREIGN PATENT DOCUMENTS

| | | |
|---|---|---|
| CN | 107700458 A | 5/2019 |
| CN | 208888043 U | 5/2019 |
| JP | 2010054467 A | 3/2010 |

\* cited by examiner

DEVICE FOR MEASURING STRENGTH AND STRAIN SOFTENING PARAMETERS OF SATURATED CLAY SAMPLE BASED ON FULL-FLOW PENETRATION

TECHNICAL FIELD

The present invention belongs to the technical field of geotechnical, geological and environmental research, and relates to a device for measuring strength and strain softening parameters of a saturated clay sample based on full-flow penetration.

BACKGROUND

Measurement of seabed soil strength parameters is the basis of marine geotechnical design and analysis. With the increase of deep-sea petroleum development and ocean engineering, to reasonable design and stability evaluation of engineering facilities such as oil and gas drilling platforms, pipelines and submarine cables, the field tests and laboratory tests, or their coordination are the main methods to estimate soil parameters in practical engineering. Field sampling as a part of marine geologic survey is one of the important way to obtain the sample of the marine soil. How to quickly, continuously, accurately and comprehensively measure the soil strength parameters for field samples is an important test both for methods and equipment.

At present, full-flow penetrometer is a key tool in the laboratory to measure the strength of soil samples. In the process of cyclic penetration and extraction of the full-flow penetrometer (such as T-bar and Ball-bar), based on the measured resistance of the penetrometer, the undrained shear strength, the strain softening parameters, and the fully remolded strength are finally estimated through the approximate linear relationship between the resistance and the strength of the soil. Compared with a vane test, the full-flow penetration test has the advantages of high measurement speed, simple, continuous strength profile, and the ability to measure the strain softening parameters of soil. As a result, the full flow penetrometer is widely used in the measurement of marine soft clay in recent years. The test results have been verified by the methods such as triaxial compression tests, direct shear tests, ring shear tests and field vane tests (FVT). Core samples are important for field investigation. The length of the samples ranges from a few meters to tens of meters. The diameters of the samples are 7.5 cm, 10 cm, 12.5 cm or other sizes. As the soil samples with a length of several meters, it is nearly impossible to obtain a continuous soil strength with depth only by performing a single penetration test. As a result, the obtained core samples are generally segmented and then measured separately in the laboratory. However, as the higher soil strength and manually eliminated overlying pressure on the segmented soil samples, a cavity would be formed during the process of the full-flow penetrometer penetration. Under this condition, the soil strength parameters cannot be accurately measured. Therefore, in the process traditional penetration tests, the method by applying a certain overlying pressure on the surface of soil sample is effectively to ensure the penetrometer under the full flow mechanism, and then the soil strength and the strain softening parameters can be tested by cyclic penetration and extraction.

The working mechanism the traditional consolidometer is based on lever. The overlying pressure on the soil samples is by adding the weights on the end of the lever. As the advantages of simple structure and easy to operate, the consolidometer is widely used in laboratory tests. Therefore, combined with the measurement principle of the full-flow penetrometer, and the overlying pressure is applied in a lever-loading method on the test soil, the full-flow penetrometer can be used to measure the high-strength saturated soil, which has great significance to the measurement of soil strength parameters. The purpose to invent this test device is to improve the application range of the full-flow penetrometer to measure the high strength soil such as the over-consolidation soil samples in laboratory and the core samples from marine field investigation. The continuously profile for the peak strength, the strain softening parameters, and the fully remolded strength would be obtained by this device.

SUMMARY

As the full flow mechanism is difficult be built in testing a segmented soil sample by a full-flow penetrometer, controllable overlying pressure is applied in a manner similar to a traditional consolidometer by the present invention to realize quick measurement of the peak strength, the strain softening parameters and the fully remoulded strength of the soil sample, so as to provide reliable strength parameters for design and stability evaluation of facilities such as pipelines and ocean foundations.

The technical solution of the present invention is as follows:

A device for measuring strength and strain softening parameters of a saturated clay sample based on full-flow penetration is mainly composed of two parts: an overlying pressure loading system I and a full-flow penetration system II.

The overlying pressure loading system I comprises a test workbench 1, a lever pressure conversion device 2, a load weight 3, an annular pressurizing frame 4, a force transmission shaft 5, an annular steel ring 6, a full-flow penetrometer 7, a cylindrical rigid box 8, a rigid box base 9, a rigid box side wall 10, a rigid box connection flange 11, a rigid box movable top cover 12, a top cover positioning rod 13, a sealable hole 14, a fixing screw 15, a drainage valve 16, geotextile 19, filter paper 20 and porous stone 21.

The test workbench 1 is placed on flat ground; the load weight 3 and a tail weight are leveled by adjusting the front end of a lever; the lever pressure conversion device 2 is installed on a table surface of the test workbench 1; and the load weight 3 is connected to the lever pressure conversion device 2.

The cylindrical rigid box 8 is placed on a top surface of the lever pressure conversion device 2; a cylindrical soil sample is placed inside the cylindrical rigid box 8; the bottom of the cylindrical rigid box 8 and the rigid box base 9 are connected by the rigid box connecting flange 11; the rigid box connecting flange 11 is fixed to the rigid box base 9 by the fixing screw 15 on the rigid box connecting flange 11; the rigid box base 9 is communicated with a drainage channel and is controlled by the drainage valve 16; the drainage valve 16 is used to control soil drainage conditions in the process of applying overlying pressure; the top of the cylindrical rigid box 8 is provided with the rigid box movable top cover 12; the rigid box movable top cover 12 is provided with the sealable hole 14 and the top cover positioning rod 13 for penetrating through the full-flow penetrometer 7; the positioning rod 13 is used to fix the installation and removal of the annular steel ring 6 and the rigid box movable cover 12; the sealable hole 14 is used to prevent the soil from being extruded during the penetration and extraction of the full-flow penetrometer 7; the annular steel ring 6 is fixed to the rigid box movable top cover 12; the annular pressurizing frame 4 and the annular steel ring 6 are connected by four steel rods; the lever pressure conversion device 2 is connected with the annular pressurizing frame 4 through the force transmission shaft 5; both ends of the annular pressurizing frame 4 are provided with through holes for the force transmission shaft 5 to pass through, and the middle is provided with through holes corresponding to the sealable hole 14 and the top cover positioning rod 13 of the full-flow penetrometer 7; the filter paper 20, the geotextile 19, the porous stone 21, the filter paper 20, the geotextile 19 and the rigid box movable top cover 12 are respectively laid on the cylindrical soil sample from top to bottom; the full-flow penetrometer 7 and the cylindrical rigid box 8 are assembled; the weight of the load weight 3 is adjusted; and pressure is applied on the soil sample in the rigid box through the annular pressurizing frame 4.

The full-flow penetration system II comprises a full-flow penetrometer 7, a loading and data collecting system 17 and a full-flow penetrometer bracket 18; the full-flow penetrometer bracket 18 is placed on the top surface of the test workbench 1; a shaft of the full-flow penetrometer 7 is connected with a loading motor on the full-flow penetrometer bracket 18; and a load cell is installed on the top of the probe to measure resistance of the probe during cyclic penetration and extraction. The full-flow penetrometer 7 is a miniature full-flow penetrometer designed for small soil samples. The probe, the shaft and the load cell have the characteristics of high accuracy and low requirements for the size of the soil samples, and have good applicability for test soil samples. The loading and data collecting system 17 includes a loading motor, a load cell, a stable power, a computer to data collection; the motor is used to control the penetration and extraction speed of the shaft of full-flow penetrometer 7 to reduce the influence of the penetration speed on the measurement of the soil strength; the signal of the load cell is collected in a test process, and the soil strength is finally estimated by the relationship between the measured pressure signal and the soil strength.

The beneficial effects of the present invention are as follows: the device of the present invention is suitable for the measurement of the soil strength and the softening parameters of the core samples from field investigation and high-strength clay consolidated in a laboratory. The test results can be used to estimate the soil strength and the strain softening parameters of the test soil, which finally providing reliable strength parameters for design and safety evaluation of engineering facilities. In the process of the full-flow penetrometer penetration, a lever loading device is used to apply the overlying pressure to the soil sample, thereby the problem of incomplete backflow of the full-flow penetrometer in the high-strength soil is solved. The test device of the present invention improves the traditional penetrometer, and applies the overlying pressure to the soil sample by using the lever loading device, thereby the full-flow mechanism is built in process of the full-flow penetrometer penetration and extraction. The application range of the full-flow penetrometer is expanded to the measurement of the high-strength soil.

Figure 1:
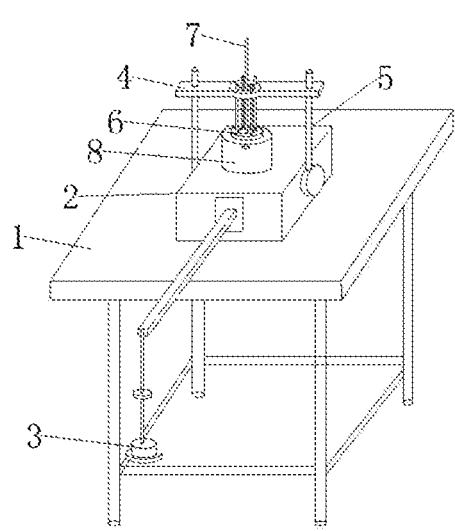
FIG. 1(a) is a layout diagram of an overlying pressure loading system of the present invention.
FIG. 1(b) is a module layout diagram of a full-flow penetration system of the present invention.
Figure 1:
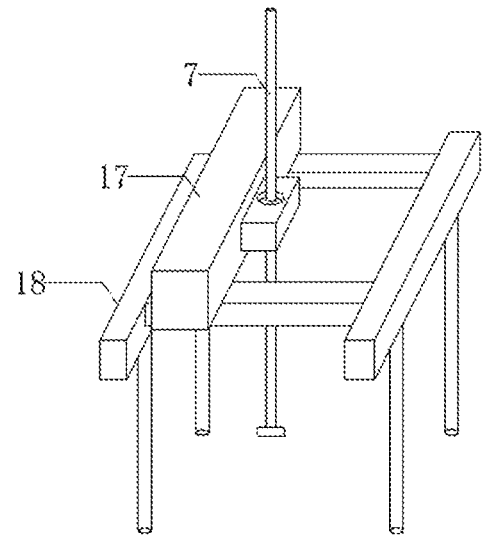
Figure 2:
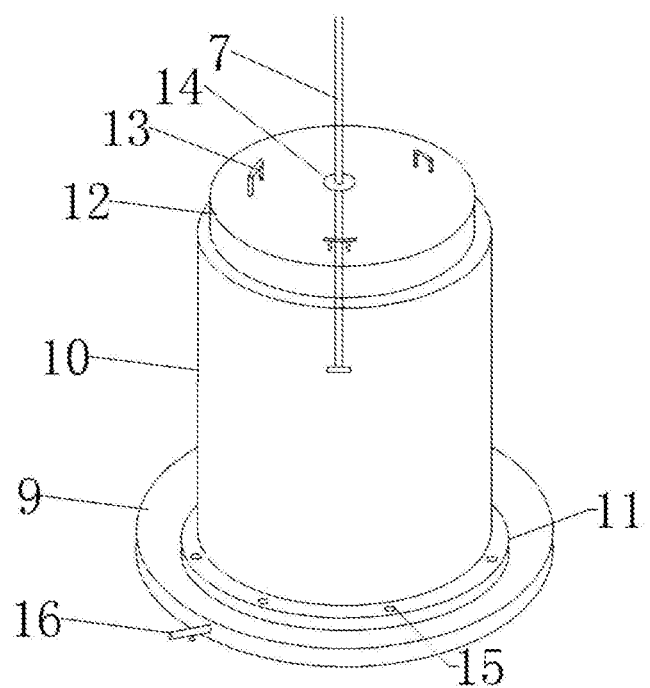
FIG. 2 is a layout diagram of a cylindrical rigid box of the present invention.
Figures 3A, 3B:
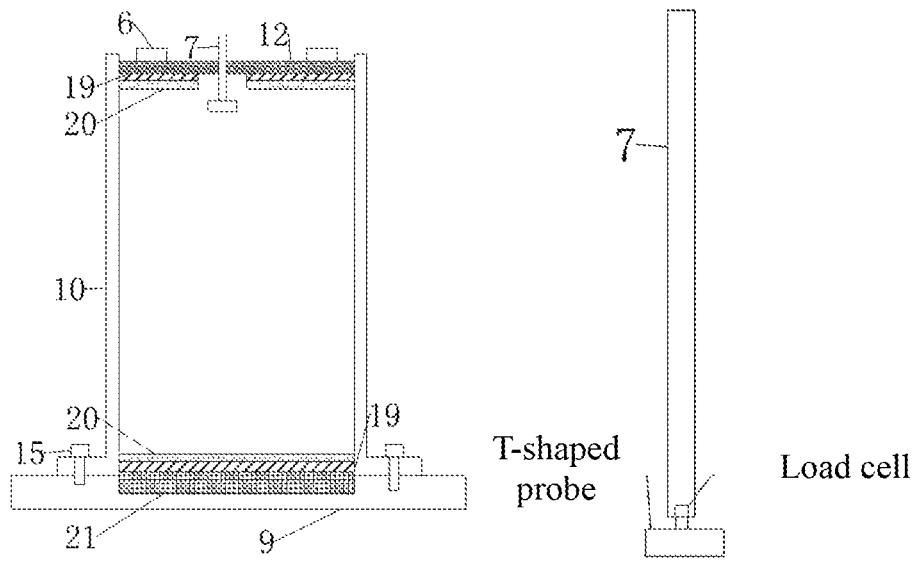
FIG. 3(a) is a sectional diagram of a cylindrical rigid box of the present invention.
FIG. 3(b) is a structural diagram of a shaft of a full-flow penetrometer of the present invention.
Figure 3C:
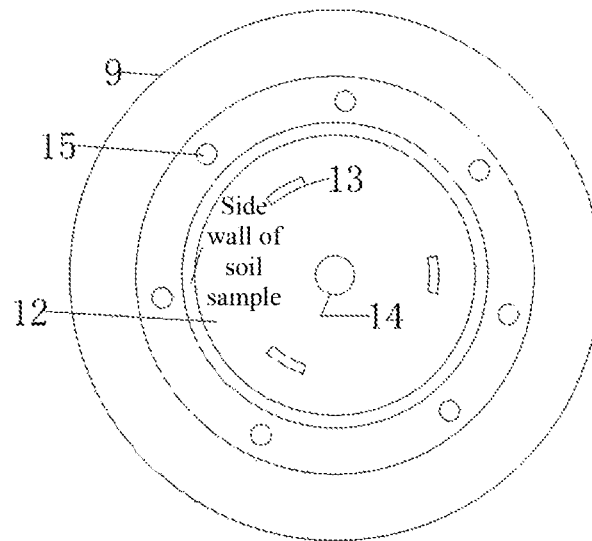
FIG. 3(c) is a top view of a cylindrical rigid box of the present invention.
Figure 4:
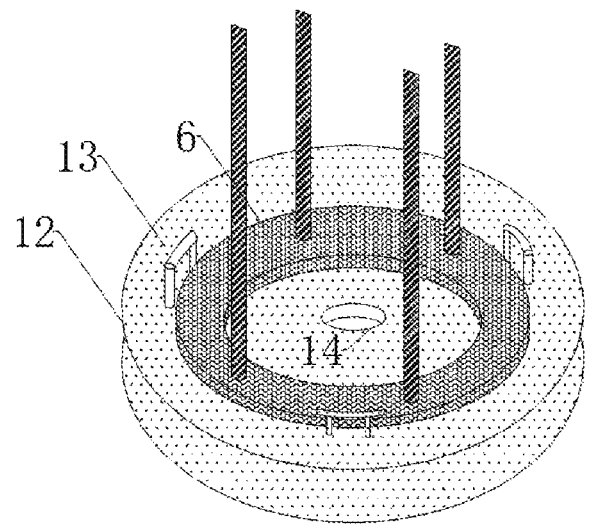
FIG. 4 is a detailed diagram of contact between a top cover of a rigid box and an annular pressurizing steel ring in the present invention.
Figure 5:
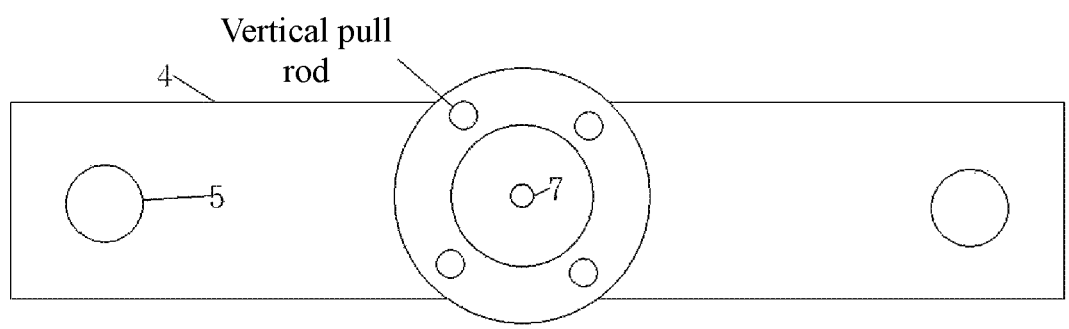
FIG. 5 is a top view of an annular pressurizing frame of the present invention.

In the drawings: 1 test workbench; 2 lever pressure conversion device; 3 load weight; 4 annular pressurizing frame; 5 force transmission shaft; 6 annular steel ring; 7 full-flow penetrometer; 8 cylindrical rigid box; 9 rigid box base; 10 rigid box side wall; 11 rigid box connecting flange; 12 rigid box movable top cover; 13 top cover positioning rod; 14 sealable hole; 15 fixing screw; 16 drainage valve; 17 loading and data collecting system; 18 full-flow penetrometer bracket; 19 geotextile; 20 filter paper; and 21 porous stone.

DETAILED DESCRIPTION

The specific embodiments of the present invention are described below in detail in combination with the technical solutions and the drawings.

EMBODIMENTS

Firstly, the test device is assembled. The workbench 1 is placed on flat ground; the overlying pressure loading system is leveled; the porous stone, the geotextile and the filter paper are laid on the bottom of the rigid box in sequence, and an appropriate amount of distilled water is added into the rigid box to ensure that a water surface is higher than the filter paper by a certain height; the drainage valve 16 is turned on; the drainage valve 16 is turned off when the water flows out; the gas below the water surface is drained; a cylindrical soil sample to be tested is cut according to the size of the rigid box and placed in the rigid box 8, and then saturated filter paper with holes of the size like the probe and the geotextile are respectively placed from bottom to top; the shaft of the full-flow penetrometer 7 penetrates through the sealable hole 14 of the top cover and stands on the soil surface; the annular pressurizing frame 4 and the annular steel ring 6 are connected through steel rods and adjusted to 2 cm on the top surface of the rigid box movable top cover 12; and cyclic penetration and extraction tests are prepared.

Then, vertical pressure is applied to the soil sample. After the device is assembled, under the condition that the vertical pressure is not loaded, by controlling the loading and data collecting system 17, the full-flow penetrometer penetrates into the soil sample surface by a distance of 2 times the diameter of the probe and then stops penetrating. The penetration resistance is collected in the process full-flow penetrometer, which provide the reference to the following cyclic penetration tests. The top cover of the cylindrical rigid box 8 is placed on the soil surface, and the annular steel ring 6 is adjusted to the surface of the rigid box movable top cover 12 to ensure the uniform contact. According to the pre-determined pressure, the weight is applied to the design load.

Finally, the cyclic penetration and extraction tests are formally conducted by using the full-flow penetrometer. After the overlying pressure reach the design value, the full-flow penetrometer is used to perform the cyclic penetration and extraction tests on the sample soil. The penetration speed is set according to the purpose. Without considering the strain rate, the penetration speed is 0.1 D/s (D is the diameter of the probe). Considering the influence of the strain rate on the soil strength, different penetration rates can be designed according to the test requirements. The full-flow penetrometer continues penetration based on the initial penetration depth, and stops the penetration at a distance of 2 cm from the surface of the soil sample. For the softening characteristics of marine clay, at least 10 cycles of penetration and extraction are performed in the middle of the soil sample. The interval range of penetration and extraction is above 5 cm. After the last cycle is ended, the soil sample is unloaded, the pressurizing frame and the top cover are removed, and a next group of tests are prepared. After the test is completed, the table is cleaned, and data processing is conducted. Analyze the problems and the deficiencies encountered in the test, and prepare the subsequent tests.

The invention claimed is:

1. A device for measuring strength and strain softening parameters of a saturated clay sample based on full-flow penetration, wherein the device for measuring strength and strain softening parameters of a saturated clay sample comprises two parts: an overlying pressure loading system I and a full-flow penetration system II;

the overlying pressure loading system I comprises a test workbench, a lever pressure conversion device, a load weight, an annular pressurizing frame, a force transmission shaft, an annular steel ring, a full-flow penetrometer, a cylindrical rigid box, a rigid box base, a rigid box side wall, a rigid box connection flange, a rigid box movable top cover, a top cover positioning rod, a sealable hole, a fixing screw, a drainage valve, geotextile, filter paper and porous stone;

the test workbench is placed on flat ground; the load weight and a tail weight are configured to be leveled by adjusting a front end of a lever; the lever pressure conversion device is installed on a table surface of the test workbench; and the load weight is connected to the lever pressure conversion device;

the cylindrical rigid box is placed on a top surface of the lever pressure conversion device; a cylindrical soil sample is placed inside the cylindrical rigid box; a bottom of the cylindrical rigid box and the rigid box base are connected by the rigid box connecting flange; the rigid box connecting flange is fixed to the rigid box base by the fixing screw on the rigid box connecting flange; the rigid box base is communicated with a drainage channel and communication between the rigid box base and the drainage channel is configured to be controlled by the drainage valve; the drainage valve is configured to control soil drainage conditions in a pressurization process; a top of the cylindrical rigid box is provided with the rigid box movable top cover; the rigid box movable top cover is provided with the sealable hole and the top cover positioning rod for penetrating through the full-flow penetrometer; the positioning rod is used to fix installation and facilitate removal of the annular steel ring and the rigid box movable cover; the sealable hole is configured to prevent the soil sample from being extruded during penetration and extraction of the full-flow penetrometer; the annular steel ring is fixed to the rigid box movable top cover; the annular pressurizing frame and the annular steel ring are connected by four steel rods; the lever pressure conversion device is connected with the annular pressurizing frame through the force transmission shaft; two ends of the annular pressurizing frame are provided with through holes for the force transmission shaft to pass through, and a middle of the annular pressurizing frame is provided with through holes corresponding to the sealable hole and the top cover positioning rod of the full-flow penetrometer; the filter paper, the geotextile and the porous stone are respectively laid on a top and a bottom of cylindrical soil sample from inside to outside; the rigid box movable top cover is located on the porous stone on top of the cylindrical soil sample; the full-flow penetrometer and the cylindrical rigid box are assembled; a weight of the load weight is adjustable; and pressure is applied to the soil sample in the rigid box through the annular pressurizing frame;

the full-flow penetration system II comprises the full-flow penetrometer, a loading and data collecting system and a full-flow penetrometer bracket; the full-flow penetrometer bracket is placed on a top surface of the test workbench; a shaft of the full-flow penetrometer is connected with a loading motor on the full-flow penetrometer bracket; a load cell is installed on a top end of a probe to measure penetration resistance of the probe during cyclic penetration and extraction; the loading and data collecting system is in electrical communication with the loading motor, the load cell, a power supply for power distribution and voltage stabilization, and a computer; the loading motor is configured to control the penetration and extraction speed of the full-flow penetrometer; a signal of the load cell is configured to be collected in a test process; and the device is configured to estimate the soil sample strength based on a measured pressure signal of the load cell.

* * * * *